(12) United States Patent
Karapetyan

(10) Patent No.: US 8,808,001 B1
(45) Date of Patent: Aug. 19, 2014

(54) METHOD AND DEVICE FOR DENTAL IMPLANT INSTALLATION

(76) Inventor: Armen Karapetyan, Los Angeles, CA (US)

(*) Notice: Subject to any disclaimer, the term of this patent is extended or adjusted under 35 U.S.C. 154(b) by 102 days.

(21) Appl. No.: 13/374,148

(22) Filed: Dec. 14, 2011

Related U.S. Application Data (62) Division of application No. 12/803,517, filed on Jun. 29, 2010, now Pat. No. 8,226,409.

(51) Int. Cl.
*A61C 8/00* (2006.01)
(52) U.S. Cl.
USPC ......................................... 433/173
(58) Field of Classification Search
USPC ............... 433/172–176, 215, 218; 604/96.01, 604/103, 104, 107–109; 606/190–192; 128/898; 623/23.67
See application file for complete search history.

(56) References Cited

U.S. PATENT DOCUMENTS

| | | | | |
|---|---|---|---|---|
| 4,762,127 | A | * | 8/1988 | Narayanan et al. ............ 606/156 |
| 4,808,165 | A | * | 2/1989 | Carr ............................ 604/97.02 |
| 6,135,771 | A | * | 10/2000 | Dragan et al. .................. 433/90 |
| 2008/0269674 | A1 | * | 10/2008 | Stone .............................. 604/80 |

* cited by examiner

*Primary Examiner* — Yogesh Patel (57) ABSTRACT

This invention, method and device for dental devices for implant installation, provides the tissue regeneration especially bone augmentation for dental implant during surgical placement of the dental implants in the grown maxillary jaw bone in order to obtain adequate volume of osseous structure by addition of the artificial bone graft material. An improved device for dental devices for implant installation comprises a blowing (pumping) means including the resting means, rod, piston, cylindrical body with cylindrical body compartment, handle, threaded cylindrical projection, and passage. Also, an improved device for dental implant installation comprises a conic nozzle or conic nozzle with balloon or nozzle with the suction clipping means, each of which includes a substance channel.

1 Claim, 5 Drawing Sheets

METHOD AND DEVICE FOR DENTAL IMPLANT INSTALLATION

CROSS-REFERENCE TO RELATED APPLICATION

This is a Divisional Application of U.S. patent application Ser. No. 12/803,517, filed Jun. 29, 2010 now U.S. Pat. No. 8,226,409.

FIELD OF THE INVENTION

The invention relates to the dental devices for implant installation, and more particularly, to the method and dental devices for tissue regeneration especially bone augmentation for dental implant. Specifically, to the method and devices which are related to the surgical placement of the dental implants in the maxillary jaw bone. Still more specifically, this invention relates to the growing of jaw bone in order to obtain adequate volume of osseous structure.

BACKGROUND OF THE INVENTION

The successful placement of the dental implants has been well known for many years, however, the success of the dental implants has been limited by the quality and quantity of existing bone a given patient would present with. As it is known, due to the destructive nature of dentures to the underlying jaw bone as well as to the fact that bone that is not internally stimulated by tooth roots will atrophy, the amount of bone in many people is very limited for the placement of dental implants. For example, individual tooth implants have been successfully carried out, and this procedure is now relatively common. However, this process may not be suitable for many dental patients due to a lack of available bone.

Also, as it is known, bone grafting has become an essential element for the successful treatment of those who do not have enough bone for dental implants. There are known methods, when blocks of hip bone have been affixed to the jaw, and freeze-dried demineralized bone protein has been used as a stimulant to cause the patient's bone cells to become active and lay down new bone onto the existing bone areas and into the new bone graft areas. Through the known experience and research, it has become evident that, for bone grafting to be successful, it must be given an isolated space to grow, protected from muscular pressure, tissue impingement and chewing forces. In order to create this space, many approaches have been proposed.

There has been developed an advanced dental technique which may permit those patients who have insufficient bone structure to reliably receive and hold support posts to still enjoy the benefit of detachable dentures or a fixed coupled to such support posts or artificial tooth. This known technique, which is presently outside the mainstream of dentistry, employs a maxillary and/or mandibular framework emplaced sub-periosteal, but resting on the existing bone structure with the denture support posts depending from a bar carried at the apex of each framework. Implants of this type have had good success, particularly when made in the mandibular position, but are subject to important objections, particularly as used in the maxillary position because of inter alia.

One known reason for the limited acceptance of sub-periosteal implants is the broad perception that the implant has a high degree of framework strut exposure which is a result of a lack of bone attachment to and around the struts as well as unsatisfactory soft tissue healing. As a result, the implants, particularly in the maxillary position, are sometimes subject to infection.

For example, the U.S. Pat. No. 6,030,218 describes a sub-periosteally implantable prosthesis support structure for a fixed or detachable dental prosthesis includes a framework fitted to and generally conforming to the inner and outer contours of the bony ridge structures of a person. The framework is configured to provide a space extending generally normal to the bony ridge structure to an apex to provide space for subsequent bone growth. A plurality of denture support posts are distributed about the framework and depend outwardly from the apex in substantial alignment with the bony ridge structure. During the fabrication of the prosthesis support structure, a biocompatible fine mesh screen is fixed to and spans, tent-like, the framework to substantially overlay the bone structure and the space provided for subsequent bone growth. After the support structure has been implanted, the growth of bone into the space and around the support structure is promoted to osseo-integrate the support structure with the person's bony ridge, thus providing a secure foundation for a denture or fixed dental prosthesis configured for detachable or fixed coupling with the denture support posts.

The sub-periosteally implantable dental prosthesis support structure for a fixed or detachable dental prosthesis which includes a framework fitted to and generally conforming to the inner and outer contours of the maxillary (and/or mandibular) bony ridge structures of a person.

Specifically, the prosthesis support has been surgically placed against and overlaying the patients maxillary bony ridge and beneath the adjacent soft tissue (e.g., gum tissue). The gum tissue is separated from the bony ridge by at least the thickness of the struts making up the framework, a condition which has been found conducive to the encouragement of subsequent bone growth.

The device includes the screen which overlays and is fixed to the framework with the support posts depending downwardly from the framework. The screen is fabricated from any bio-compatible material suitable as to strength and appropriate for permanent retention in the mouth of an individual. The purpose of the screen is to create a tenting of the gum tissue above the bone in order that bone will grow between and to the frame and into the weave. In addition, it serves to provide a rigid, bio-compatible structure for the gum tissue to become attached in its new, tented position.

The framework is covered with a mesh screen to effect a complete prosthesis support structure for use in the mandibular position. The screen, may be fabricated from any material suitable as to strength and appropriate for permanent retention in the mouth of an individual, and the presently preferred material is titanium, the alternative materials having been discussed above. The framework is made of a suitable material, such as titanium stock, for lightness and strength as well as appropriateness for permanent emplacement in a patient's mouth. Similarly, the mesh may be attached to the framework by any suitable means such as with an adhesive or by welding, spot welding being particularly suitable when the presently preferred material, titanium, is used, or by sintering or even by the use of suitably placed ligatures.

The mesh should be sufficiently open as to permit nutrients to readily pass to the underlying tissue, but strong enough to establish a relatively rigid structure in use. It has been found that, when titanium mesh is employed, on the order of 0.003 inch wire in about a 50.times.50 wires per inch weave is a very suitable mesh for the intended purpose. The titanium stock from which the frameworks are fabricated can be on the order of 0.050-0.200 inch thickness (the presently preferred method of fabricating the frame is as a one-piece casting).

Such principles, used for dental implant installation, are not reliably efficient and create an external extended ridge providing complexity of leveling of the original teeth with the artificial (implanted) tooth. Also, such method requires the separation of gum.

The same deficiencies inherent in the Patent Application Publication No. US2001/0012607 describes a method of growing additional maxillary (or mandibular) bone in areas of atrophy and by the use of a related device to accomplish the task. A pliable guided-tissue regeneration plate, which holds it shape after being bent, is employed as a mating component to a support screw or a dental implant and is secured to the jaw structure by fixation of the guided-tissue regeneration plate at a predetermined distance above or away from the surface of the bone to the support screw or dental implant in order to create a supported and protected space between the underside of the gum tissue and the original bone which is free from muscular and chewing pressure in order to promote bone growth.

The guided-tissue regeneration plate support and fixation system can be mated with a support screw or screws which are tenting screws designed to be mated with and then become intimately a part of the guided-tissue regeneration plate in order to grow bone in the space created by the guided-tissue regeneration plate system prior to implant placement. Additionally, the guided-tissue regeneration plate system can be utilized during implant placement by creating space adjacent to a dehisced implant by fixation of the guided-tissue regeneration plate directly to the implant in order to grow bone height or width. A guided-tissue regeneration plate according to the present invention can also be used by affixing it to an existing dental implant that has been previously placed and has undergone bone loss in order to regenerate new bone. The guided-tissue regeneration plate support and fixation system is adapted to be surgically removed after the bone has grown under its surface at a later uncovering or implant placement surgery. In an alternative preferred embodiment which provides particularly successful results and which results in faster and better bone regeneration and periosteum growth, the guided-tissue regeneration plate consists of first and second integrated components including a first support plate component having a peripheral region and a generally open central portion and a fine mesh screen juxtaposed over the central portion and fixed to the peripheral region thereof. In a functionally equivalent variant of the alternative preferred embodiment, the guided-tissue regeneration plate is fabricated starting with an imperforate plate (for example, of titanium) and then reducing the thickness of predetermined central regions of the plate, a step which can be carried out, for example, by employing a conventional photoresist mask over the plate in conjunction with an acid etch. After the desired thickness of the central regions has been obtained, the central regions may be perforated with finely spaced apertures using, for example, conventional laser machining techniques.

Specifically, the invention uses guided-tissue regeneration plate which has been molded, then bone graft material is packed beneath the plate and against the existing bony ridge. After a period of approximately four-to-eight months, a new bony ridge will form within the space created by the guided-tissue regeneration plate support, its fixation system, and the cortical bone (more precisely, the gum tissue). In order to place a guided-tissue regeneration plate support and fixation system according to the present invention, the tissue is first reflected away from the bony ridge to expose the ridge in its entirety. The palatal gum tissue is reflected, the facial gum tissue is reflected, and a guided-tissue regeneration plate support screw is placed into the bony ridge. Later the guided-tissue regeneration plate support and fixation system has been removed exposing the new bony ridge (a small hole remains after the removal of the guided-tissue regeneration plate support screw) and implant can be placed (installed) into the new bony ridge (a tooth can be attached to the implant later).

Such method may easily traumatize the tissue.

The U.S. Pat. No. 7,396,232 describes the method and device for periosteal distraction. The device by this patent uses as jack placed beneath the periosteum through a small incision. This jack lifts the Schneiderian membrane. When the periosteum reached the desired dimension the jack is taken out and a bone graft is placed as described above. For instance, FIG. 15B of the mentioned above patent shows a preferred embodiment using the final dental implant as the elevating screw (jack). The preferably tapered implant 200 with preferably round apical region and preferably threads along the body of the implant is inserted through the alveolar ridge to reach the Schneiderian membrane 146. The implant is protruding through the gums 201 to the oral cavity. Over the implant 200 a tube 202 is placed reaching the alveolar bone 147.

This method allows to avoid the necessity to stretch the mucoperiosteal tissue therefore reducing the complications: The methods to regenerate the bone are well known. The known methods use the distraction osteogenesis, which is a process whereby bone is stretched to increase bone volume. According to distraction osteogenesis processes, at least one portion of a bone is at least partially separated from the bone. The position of the portion is gradually altered with respect to the bone. Time is then provided for new bone to fill in the space between the portion and the overall bone.

When distraction osteogenesis is used in dentistry dental applications, a portion of a patient's jawbone will be at least partially severed from the overall jawbone. The jawbone segment may then be gradually separated from the rest of the jawbone. New bone then fills in the space between the segment and the jawbone. By increasing the volume of bone in the jawbone, additional area can be provided to anchor or at least more securely anchor dental implants. Distraction osteogenesis can also be used in dental applications simply to strengthen a location on the jawbone to increase the bone volume at that location even if implants are not to be secured in the jawbone at that location.

These techniques of distraction osteogenesis has the known disadvantage, i.e., this procedure can be done if the height of the ridge is at least 6 mm.

The U.S. Pat. No. 7,396,232 allows the distraction osteogenesis without cutting a segment of the bone therefore the procedure is simple minimal invasive and not traumatic. In this invention the Schneiderian membrane is separated from the bone by the jack (by the dental implant as the elevating screw).

This method uses the tooth cannel to elevate the Schneiderian membrane. The another very important deficiency of this method is the use of the mechanical jack (the dental implant as the elevating screw (jack)). The Schneiderian membrane is a very sensitive and thin membrane for mechanical instruments, even such as screw. Additionally, the most dental implants (specifically screw-type dental implants) have the very sharp (screw-type) free end of the implant, which can easily traumatize and even injury the Schneiderian membrane.

Therefore, the mentioned known methods and devices have the described above deficiencies which are eliminated in the improved device for dental implant installation.

While the mentioned above prior art fulfill their respective, particular objectives and requirements, the mentioned inventions do not disclose, teach and/or suggest the device for dental implant installation including the elements (components/parts) inflating its/their capacity/volume to securely move the Schneiderian membrane providing internal place for the material grafting the artificial bone(s).

Those skilled in the art will readily observe that numerous modifications and advantages of the improved device for dental implant installation may be made while retaining the teachings of the invention.

Thus, the known prior art do not provide the efficient, satisfied, convenient (without gum separation) device for dental implant installation according to the present invention substantially departs from the devices of the prior art.

OBJECT AND ADVANTAGES OF THE INVENTION

Accordingly, several objects and advantages of the present invention are to provide the improved method and device for dental implant installation:

It is another object of the invention increase the safety of the Schneiderian membrane during dental procedure of displacing (elevating) the Schneiderian membrane.

It is further object of the invention to minimize the possible traumatization of the Schneiderian membrane during displacement (elevation) of the Schneiderian membrane.

It is still another object of the invention to increase the convenience and efficiency of the dental implant installation method and the device realizing the improved method.

DESCRIPTION OF THE DRAWING

In order that the invention and the manner in which it is to be performed may be more clearly understood, embodiments thereof will be described by way of example with reference to the attached drawings, of which.

SUMMARY OF THE INVENTION

In view of the foregoing disadvantages inherent in the known prior art, the present invention provides an improved method and device for dental implant installation. As such, the general purpose of the present invention, which will be described hereinafter in greater details, is to provide method and device for dental implant installation, which has many of the advantages of the dental implant installation mentioned heretofore and many novel features that result in the safety procedure with the Schneiderian membrane, which is not anticipated, rendered obvious, suggested or even implied by any of prior art methods and dental devices, either alone or in any combination thereof.

To attain this, the present invention generally comprises the method and device for the dental implant installation. An improved dental device for dental implant installation includes a blowing (pumping) means including the resting means, rod, piston, cylindrical body with cylindrical body compartment, handle, threaded cylindrical projection, and passage. Also, an improved device for dental implant installation comprises a conic nozzle or conic nozzle with balloon or nozzle with the suction clipping means, each of which includes a substance channel.

DESCRIPTION OF THE PREFERRED EMBODIMENTS

With reference now to the drawings, and particularly to FIGS. 1A-11 thereof, an improved method and device for dental implant installation embodying the principles and concepts of the present invention.

Figures 1A, 1B, 1C:
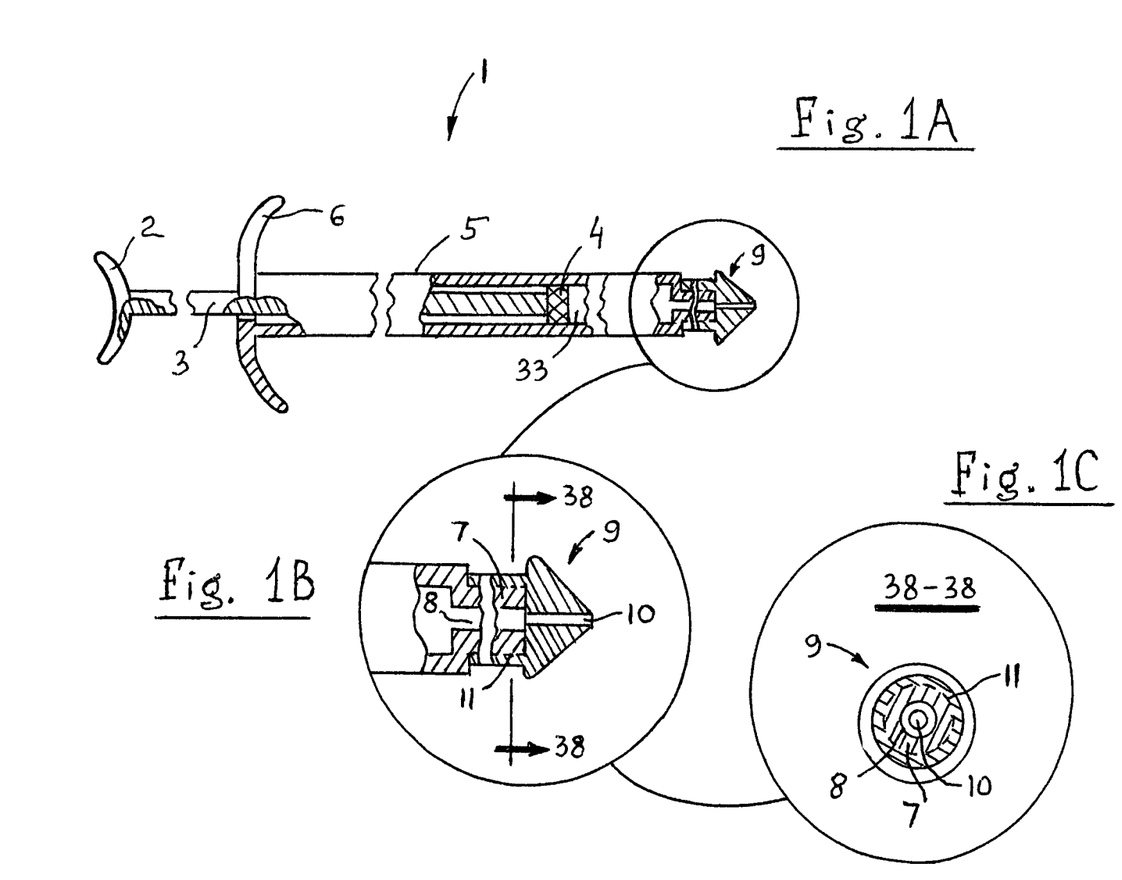
FIG. 1A is a simplified drawing of the improved device.
FIG. 1B is a magnified portion of the FIG. 1A.
FIG. 1C is a simplified cross-sectional view of the portion of the improved device.

Referring to FIG. 1A, an improved device for dental implant installation comprises a blowing (pumping) means 1 including the resting means 2, rod 3, piston 4, cylindrical body 5, handle 6, cylindrical projection 7, passage 8. The resting means 2 and rod 3 may be one solid piece, as it is shown in FIG. 1A, or may be of configuration of two separate pieces coupled to each other. The rod 3 is also coupled with the piston 4.

Also, an improved device for dental implant installation comprises a conic nozzle 9, including a substance channel 10. The cylindrical projection 7 of the blowing means 1 includes a thread 11 (the outer thread), and the outer diameter of the cylindrical projection 7 is smaller than the outer diameter of the cylindrical body 5.

Figure 2:
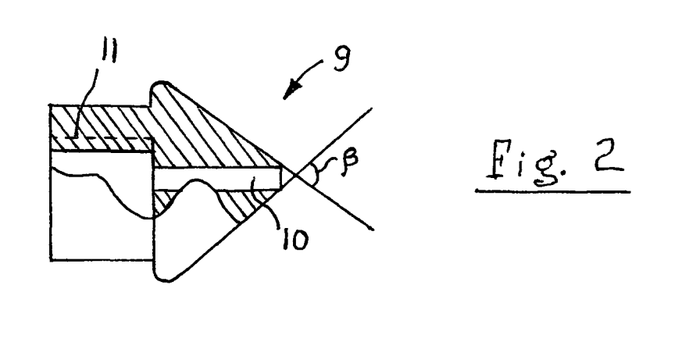
FIG. 2 is a simplified drawing of the conic nozzle.
Figure 3:
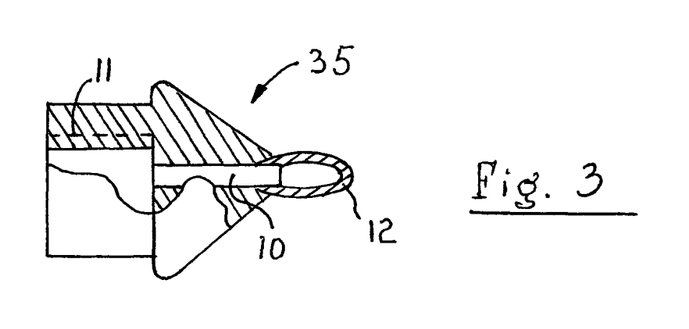
FIG. 3 is a simplified drawing of the conic nozzle with the balloon.

The conic nozzle 9 includes a thread 11 (the inner thread), as it is shown in FIGS. 2 and 3.

The threaded coupling of the blowing means 1 and conic nozzle 9 is shown, as example, in FIGS. 1A, 1B and 1C (see also FIGS. 2-4), but the other kinds of the coupling can be used. For instance, the tighten (friction) non-leaking coupling, non-leaking locking coupling, the use of sealing gaskets, etc. can be used successfully too.

The angle "β" of the intersection of conic nozzle's sides may be in the range of approximately 45°-90° (FIG. 2).

The FIG. 3 illustrates the conic nozzle 35 comprising the molded-in (glued to, etc.) balloon 12 or even extended from a vertex of the conic nozzle. Also, the balloon 12 can be securely attached (connected) to the conic nozzle 9. The balloon 12 should be attached/connected to the conic nozzle 9 by non-leaking connection (e.g., the annular groove (not shown) can be included in the area of vertex of the nozzle 9 for the balloon tail's rim (not shown), or a small (miniature) elastic hose clamp can be used, etc.).

The improved device for dental implant installation operates as follows. The improved method and device provide the growing of maxillary jaw bone (alveolar bone) in order to obtain adequate volume of osseous structure, and the installation of the dental implant in the grown maxillary jaw bone.

Figure 5:
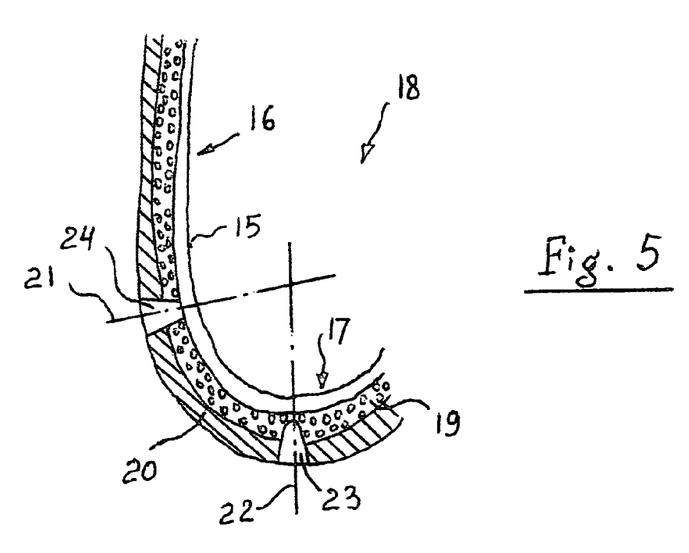
FIG. 5 is a simplified cross-sectional view of the maxillary jaw bone with opening.
Figure 6:
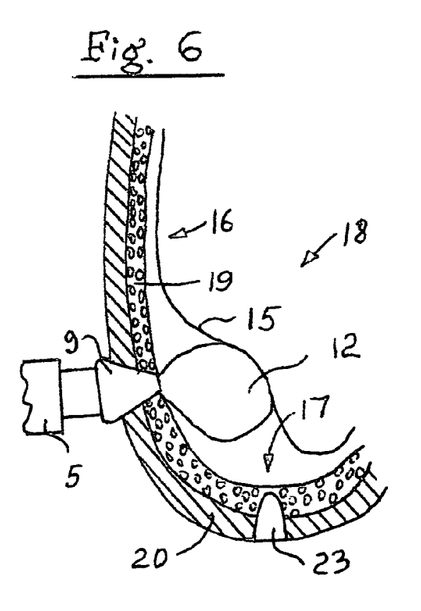
FIG. 6 is a simplified cross-sectional view of the maxillary jaw bone with the blowing means.
Figure 7:
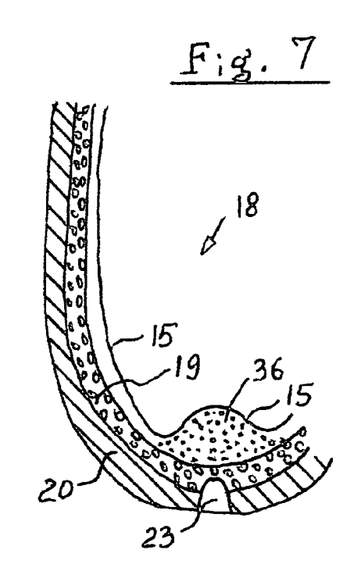
FIG. 7 is a simplified cross-sectional view of the maxillary jaw bone with the artificial bone graft material.
Figure 8:
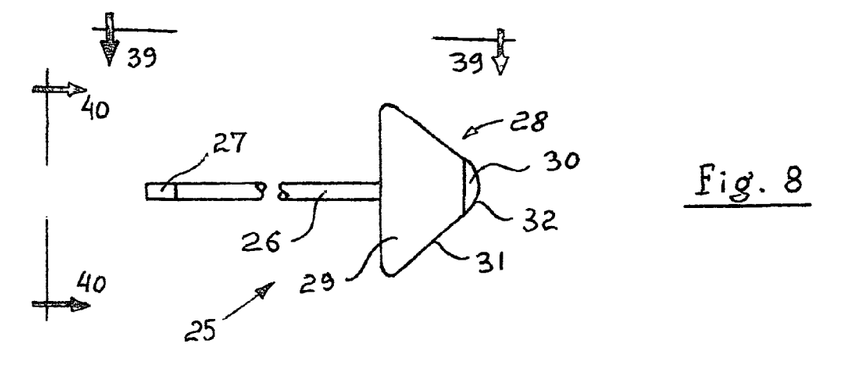
FIG. 8 is a simplified drawing of the truncated cone-type expanding means.
Figure 9:
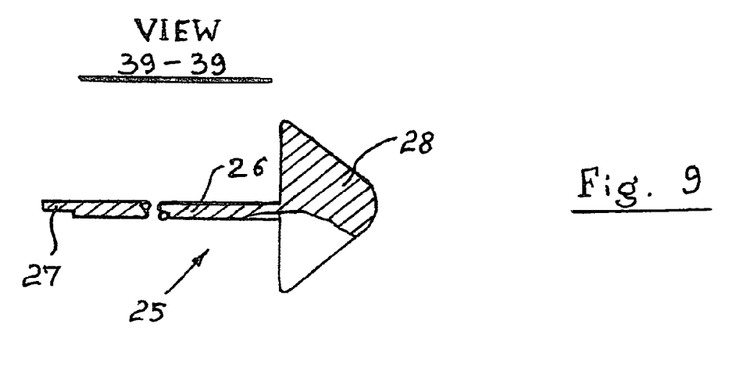
FIG. 9 is a simplified top view of the truncated cone-type expanding means.
Figure 10:
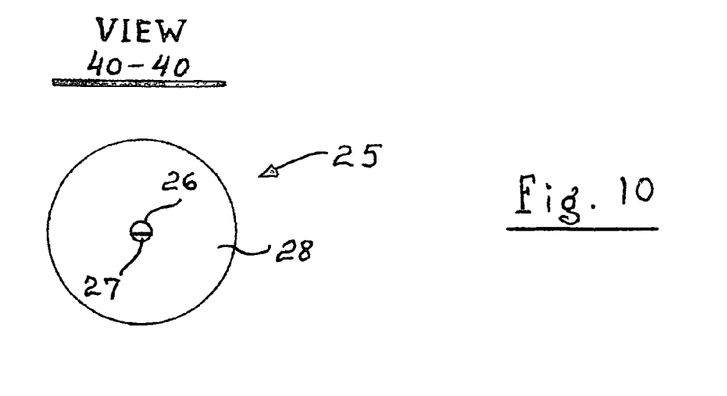
FIG. 10 is a simplified side view of the truncated cone-type expanding means.

In order to minimize the traumatization (or even injury) of the Schneiderian membrane 15, the improved method provides the safe elevation of the Schneiderian membrane 15 from the wall 16 and floor 17 of the sinus compartment 18 (FIGS. 5-7). In order to make an access to the inner side of the alveolar bone 19 of the sinus compartment 18, the aperture (not shown) in the alveolar bone 19 (through the gum 20) has to be provided (e.g., drilled) along the axis 21 in the direction crossing the axis 22 of the tooth root socket (root channel) 23 (FIG. 5). The axis 21 crosses the axis 22 of the tooth socket 23 at the angle approximately closed to the 90°, but may very from the patient to patient. The approximate perpendicular (angle closed to the 90°) intersection of the axes 21 and 22 may be explained by the fact, that the aperture (not shown) is located in the area of the wall 16 of the sinus compartment 18, but the tooth root socket is located in the area of the floor 17 of the sinus compartment 18. The intersection of the axes 21 and 22 occurs within the sinus compartment 18. The aperture (not shown) in the alveolar bone 19 (through the gum 20) along the axis 21 may be provided (e.g., drilled) by, for example, dental bore (not shown), etc. Further, the conic-type opening 24 (FIG. 5) is provided by the truncated cone-type expanding means 25. The truncated cone-type expanding means 25 comprises a rod 26 including a flange 27 (FIGS. 8-10). The flange 27 is used for the fixed installation in the dental bore-instrument (not shown), but the other dental bore-instruments, for instance, the hand drills (not shown), etc. can be successfully used for this purpose. The flange 27 may be replaced by any suitable means providing fixation of the truncated cone-type expanding means 25 into the bore-instruments (into the drilling instruments [not shown]), for example, the circular groove (not shown) with the flange can be used or a square-form flange or any other configuration can be used, etc. Also, the truncated cone-type expanding means 25 comprises the truncated cone-type head 28, which includes a truncated-cone portion 29 and a hemispherical portion 30. The truncated-cone portion 29 includes an abrasive surface 31 (FIG. 8), which used to expand the aperture (not shown) to the conic-shape opening 24 shown in FIG. 5. The different abrasiveness can be used to expand the aperture (not shown) to the conic-shape opening 24. The diamond abrasive material (not shown), etc. can be used on the abrasive surface 31. The hemispherical portion 30 includes a fine (polished) surface 32 (FIG. 8). The fine (polished) surface 32 of the hemispherical portion 30 is necessary to prevent the traumatization and injury of the thin Schneiderian membrane 15 during expanding the aperture (not shown) to the conic-shape opening 24. The stock 26 can be extended of the truncated cone-type head 28 (FIG. 9) or can be attached (not shown) to the truncated cone-type head 28

The expanding of the aperture (not shown) to the conic opening 24 has to be preferably provided by the handle drilling instrument. The hand drilling instrument is preferred considering that the any motorized dental drilling instruments may be not safe enough to avoid traumatization or even injury of the Schneiderian membrane 15 during expanding the aperture (not shown) to the conic-shape opening 24.

The conic nozzle 9, connected with the cylindrical projection 7 of the cylindrical body 5 of the blowing (pumping) means 1, is inserted in the conic-shape opening 24 (FIG. 6). The cylindrical body compartment 33 may be filled with the substance such as an air or, for instance, water. When the resting means 2 pushed toward the handle 5, the rod 3 pushes the piston 4, which provides insertion of the substance from the cylindrical body compartment 33 through the passage 8 in the cylindrical projection 7, and from cylindrical projection 7 through substance channel 10 into the sinus compartment 18. The substance elevates the Schneiderian membrane 15 from the wall 16 and floor 17 of the sinus compartment 18.

The FIG. 6 illustrates the elevation of the Schneiderian membrane 15 by the balloon 12 (see also FIG. 3), where the balloon 12 (of the conic nozzle with balloon shown in FIG. 3), placed (through the opening 24) into the sinus compartment 18, is blown by the blowing means 1. The conic nozzle with balloon is marked as 35 in FIG. 3.

The conic nozzle with balloon 35 may include the inner thread (FIG. 3) for coupling with the threaded cylindrical projection 7 of the blowing means 1, but the other kinds of the coupling can be used. For instance, the tighten (friction) non-leaking coupling, non-leaking locking coupling, the use of sealing gaskets, etc. can be used successfully too.

The conic nozzle with balloon 35, connected with the cylindrical projection 7 of the cylindrical body 5 of the blowing means 1, in the same manner as the conic nozzle 9, is inserted in the conic-shape opening 24 (FIG. 6). The cylindrical body compartment 33 may be filled with the substance such as an air or, for instance, water. When the resting means 2 pushed toward the handle 5, the rod 3 pushes the piston 4, which provides insertion of the substance from the cylindrical body compartment 33 through the passage 8 in the cylindrical projection 7, and from cylindrical projection 7 through substance channel 10 into balloon 12 inflating the balloon 12, which elevates the Schneiderian membrane 15 from the wall 16 and floor 17 of the sinus compartment 18.

Figure 4:
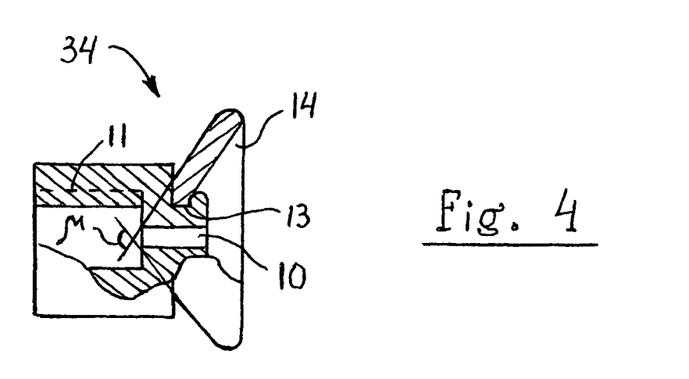
FIG. 4 is a simplified drawing of the nozzle with the suction clipping means.

The substance may be also blown (pumped) into the Schneiderian membrane 15 by the blowing means 1 coupled with the nozzle 34 shown in FIG. 4. The nozzle 34 includes a neck 13, in which the suction clipping means 14 is installed. The substance located in the cylindrical body compartment 33 follows (under pressure of the piston 4) through the passage 8 of the cylindrical projection 7 into the substance channel 10 of the nozzle 34, and from the substance channel 10 through the regular aperture (not shown) into the sinus compartment 18. The sides of the suction clipping means 14 may intersect each other at the angle "μ" having a range of approximately 60°-120° (FIG. 4). The use of the blowing means 1 with the attached nozzle 34, may not require the necessity to provide the conic opening 24, to use the truncated cone-type expanding means 25 and conic nozzle 9 (or conic nozzle with balloon 35), but may not fully eliminate the leakage of the substance in the area of the contact of the suction clipping means 14 with the gum 20. In order to avoid the leakage of the substance between the suction clipping means 14 and the gum 20, the suction clipping means 14 has to have the tight contact with the gum 20. The suction clipping means 14 may be of the circular form or, for instance, of the elongated form (e.g., such as oval or elliptical form elongated in the horizontal direction [along the alveolar bone length], etc.). The suction clipping means 14 may be made of any suitable elastic material.

The different blowing means 1 may be used to blow (pump) the substance in the sinus compartment 18. The FIG. 1A depicts the blowing means 1, which is presented by some kind of the medical syringe, but it may be the other kinds of the devices, for example, some kind of the gun-type hand pumping devices (not shown), etc.

Figure 11:
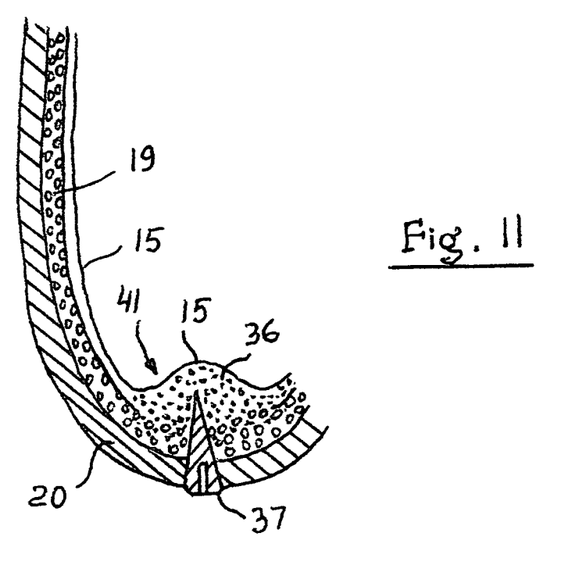
FIG. 11 is a simplified cross-sectional view of the increased volume of the maxillary jaw bone.

After the Schneiderian membrane is safely elevated from the alveolar bone 19, the blowing means 1 via the conic nozzle 9 or nozzle 34 inserts the artificial bone graft material 36 into the sinus compartment 18 between the Schneiderian membrane and alveolar bone 19 in the area of the floor 17, as it is shown in FIG. 7. After the certain time the opening 24 is naturally closed (FIG. 7), and within approximately 7-8 months, the created formation 41 of the artificial bone graft material (particles) 36 and alveolar bone 19 (FIG. 11) becomes the adequate volume of the maxillary jaw bone (of the increased maxillary jaw bone), which is ready for the dental implant installation through the tooth root channel (tooth root socket) 23 (FIG. 11).

CONCLUSION, RAMIFICATION AND SCOPE

Accordingly the reader will see that, according to the invention, I have provided an improved method and device for dental implant installation. There has thus been outlined, rather broadly, the more important features of the invention. In this respect, it is understood that the invention is not limited in its application to the details of steps, construction and to the arrangements of the components set forth in the description and/or drawings. The invention is capable of other embodiments and of being practiced and carried out in various ways. Also, it is to be understood that the phraseology and terminology employed herein are for the purpose of description and should not be regarded as limiting.

While the above description contains many specificities, these should not construed as limitations on the scope of the invention, but as exemplification of the presently-preferred embodiments thereof. Many other ramifications are possible within the teaching to the invention. For example, an improved method and device for dental implant installation can be successfully used not only for installation of the dental implants in the maxillary jaw bone, but also for installation of the dental implants in the mandibular jaw bone by growing of alveolar bone in order to obtain adequate volume of osseous structure.

As such, those skilled in the art will appreciate that the conception, upon which this disclosure is based, may readily be utilized as a basis for the designing of other structures, for carrying out the several purpose of the present invention. It is important, therefore, that the claims be regarded as including such equivalent constructions insofar as they do not depart from the spirit and scope of the present invention.

THE DRAWING REFERENCE NUMERALS

1.—a blowing means;
2.—a resting means;
3.—a rod;
4.—a piston;
5.—a cylindrical body;
6.—a handle;
7.—a cylindrical projection;
8.—a passage;
9.—a conic nozzle;
10.—a substance channel;
11.—a thread;
12.—a balloon;
13.—a neck;
14.—a suction clipping means;
15.—a Schneiderian membrane;
16.—a wall of the sinus compartment 18;
17.—a floor of the sinus compartment 18;
18.—a sinus compartment;
19.—a alveolar bone;
20.—a gum;
21.—an axis of the opening;
22.—an axis of the root socket;
23.—a tooth root socket;
24.—an opening;
25.—a truncated cone-type expanding means;
26.—a stock;
27.—a flange;
28.—a truncated cone-type head;
29.—a truncated cone portion;
30.—a hemispherical portion;
31.—an abrasive surface;
32.—a fine surface;
33.—a cylindrical body compartment;
34.—a nozzle;
35.—a nozzle with balloon;
36.—an artificial bone graft material;
37.—a dental implant;
38-38—a cross-sectional view;
39-39—a top view;
40-40—a side view;
41.—a formation of the artificial bone graft material 36 and alveolar bone 19.

What is claimed is:

1. A device configured for dental implant installation comprising:
   a blowing device including
      a resting member comprising a rod coupled with a piston;
      a cylindrical body comprising a handle and a cylindrical body compartment in which said piston is inserted;
      a cylindrical projection extended of said cylindrical body, wherein said cylindrical projection includes an outer thread and a passage for a substance located in said cylindrical body compartment between said piston and said passage;
   a nozzle coupled with said cylindrical projection of said blowing device, wherein said nozzle comprises:
      an inner thread which is coupled with said outer thread of said cylindrical projection of said blowing device;
      a neck onto which a suction clipping device is installed, wherein said suction clipping device comprising truncated cone configuration including a base of an oval or an elliptical geometric configuration, and wherein said nozzle comprises a rim portion for attaching to a gum of a patient, and wherein said oval or said elliptical configuration of said base is elongated in horizontal direction along said gum;
      a substance channel providing a passing of said substance from said passage of said cylindrical projection through an aperture into a sinus compartment, wherein sides of said suction clipping device defines an axis, respectively, which intersect each other at the angle of the range of 60°-120°.

* * * * *